(12) United States Patent
Roberts et al.

(10) Patent No.: US 8,191,430 B2
(45) Date of Patent: Jun. 5, 2012

(54) METHOD AND APPARATUS FOR PIPE TESTING

(75) Inventors: Peter Miles Roberts, Horsham (GB); Alastair Chalmers Walker, Couslden (GB)

(73) Assignee: VerdErg Ltd, Knaphill (GB)

( * ) Notice: Subject to any disclaimer, the term of this patent is extended or adjusted under 35 U.S.C. 154(b) by 155 days.

(21) Appl. No.: 12/531,874

(22) PCT Filed: Mar. 17, 2008

(86) PCT No.: PCT/GB2008/050184
§ 371 (c)(1),
(2), (4) Date: Apr. 19, 2010

(87) PCT Pub. No.: WO2008/114049
PCT Pub. Date: Sep. 25, 2008

(65) Prior Publication Data
US 2010/0212405 A1    Aug. 26, 2010

(30) Foreign Application Priority Data
Mar. 20, 2007   (GB) .................................. 0705306.9

(51) Int. Cl.
*G01S 5/06* (2006.01)
(52) U.S. Cl. .......................................... 73/807; 73/49.6
(58) Field of Classification Search ................... 73/49.5, 73/807, 821, 825
See application file for complete search history.

(56) References Cited

U.S. PATENT DOCUMENTS
3,240,207 A * 3/1966 Barker et al. ................. 600/488
(Continued)

FOREIGN PATENT DOCUMENTS
GB    1432539 A    4/1976
(Continued)

OTHER PUBLICATIONS
International Search Report, mailed Apr. 12, 2010, for PCT/GB2008/050184, 4 pages.
(Continued)

*Primary Examiner* — Freddie Kirkland, III
(74) *Attorney, Agent, or Firm* — Seed IP Law Group PLLC

(57) ABSTRACT

A method of testing pipes for use in making subsea pipelines comprises cutting a ring from one or more pipes of the type used to make the pipeline; forming flat, substantially parallel surfaces on the ends of the ring; providing means for measuring strain and deformation of the ring; mounting the ring in a pressure chamber such that the ends of the ring form seals with opposing walls of the chamber to isolate the inside of the ring from the outside; increasing the pressure outside the ring and measuring the strain and deformation on the ring as the pressure increases; and using the deformation and strain measurements to determine a wall thickness for pipes to be used for the pipeline. An apparatus for testing rings cut from pipes for use in making subsea pipelines, comprises first and second test chamber sections which, when placed together define a test chamber for receiving the ring to be tested; one or more sensors for measuring strain and deformation of the ring; sealing means located in the chamber for forming a seal against the ring when received in the chamber; means for clamping the first and second sections together to form the chamber and engage the sealing means against the ring when received in the chamber to form a pressure resistant seal between the inside and outside of the ring; and a fluid inlet port in one of the chamber sections to allow a pressurised fluid to be admitted to the chamber outside the ring when received in the chamber.

18 Claims, 4 Drawing Sheets

U.S. PATENT DOCUMENTS

| | | | |
|---|---|---|---|
| 3,331,238 A | 7/1967 | Kost et al. | |
| 3,439,381 A | 4/1969 | Plomp | |
| 3,490,525 A | 1/1970 | Nettles | |
| 3,960,018 A | 6/1976 | Change et al. | |
| 4,192,194 A | 3/1980 | Holt | |
| 4,290,311 A | 9/1981 | Brewer | |
| 4,911,004 A * | 3/1990 | Leon | 73/168 |
| 5,339,693 A * | 8/1994 | Rowlands et al. | 73/825 |
| 5,379,645 A * | 1/1995 | Smart | 73/794 |
| 6,253,599 B1 * | 7/2001 | Chang et al. | 73/49.8 |
| 6,619,104 B1 * | 9/2003 | Yeh | 73/49.6 |
| 6,854,327 B2 * | 2/2005 | Rambow et al. | 73/250 |
| 7,245,791 B2 * | 7/2007 | Rambow et al. | 385/12 |
| 2003/0110864 A1 | 6/2003 | Vujanic et al. | |
| 2006/0233482 A1 | 10/2006 | Rambow | |
| 2009/0223301 A1 | 9/2009 | Schwab | 73/825 |

FOREIGN PATENT DOCUMENTS

JP  08285749 A  11/1996

OTHER PUBLICATIONS

Written Opinion, mailed Apr. 12, 2010, for PCT/GB2008/050184, 5 pages.

Zimmermann and D. DeGeer, *Large pressure chamber tests ultra-deepwater pipe samples*, Word Oil, supplement Deepwater Technology, Aug. 1999, 19 pages.

Standards for Subsea Pipeline Design and Construction, OJSC Gazprom, Administrative Regulations, BH 39-1,9-005-98, Moscow,1998, 17 pages.

* cited by examiner

METHOD AND APPARATUS FOR PIPE TESTING

TECHNICAL FIELD

This invention relates to methods and apparatus for testing pipes such as those used for forming underwater pipelines.

BACKGROUND ART

There has been a progressive development of very deep-water reservoirs of gas and/or oil around the world. Until about 10 years ago, very deep water was defined to be any depth greater than about 1000 m. Currently however, so many pipelines have been installed in depths greater than this that the definition of very deep water is currently about 2000 m. This development in installation capability is continuing and currently pipelines in 3500 m water depth are being planned.

The pipelines are typically installed empty, i.e. filled with air at ambient pressure and only filled with oil or gas under pressure once installation is completed. A major risk experienced during the installation of these deep-water pipelines is from the pressure applied by the water causing the pipe to deform out of its initial round shape and deform into an almost flat configuration. This is called external pressure collapse and if not controlled can result in the total loss of the pipeline. The dimensions, i.e. diameter and wall thickness and to a lesser degree the material properties, of a very deep-water pipeline are therefore determined by the potential for external pressure collapse.

This is in complete contrast to the design of a conventional shallow-water or onshore pipeline where the wall thickness is sized to resist internal pressure from the fluid it is to carry rather than external pressure.

Various theoretical studies of external pressure collapse have been carried out and numerical modelling has also been used to calculate the maximum water depth at which a pipeline with specified dimensions can safely be installed. However, the consequences of external pressure collapse buckling are so great that these theoretical studies are not sufficient for confident management of the risk. Also, the most important method for reducing the potential for such local collapse, by increasing the wall thickness of the pipe, is so expensive and possibly not technically realisable, that the proposed pipeline might well not be commercially feasible. This in turn raises the possibility that the exploitation of the gas or oil reservoirs are abandoned.

The alternative to basing all design on the results from theory is to additionally carry out tests. Indeed, several tests have been carried out for a range of pipe wall thicknesses. These tests involve placing long lengths of specially fabricated pipe in special pressure chambers and increasing the external pressure until collapse occurs. Only one or two laboratories have such facilities available and the tests are very expensive, in the order of $100,000 for one test.

Codes have been prepared to provide a basis for the calculation of the dimensions for pipes that are required to operate at specified great depths. These codes encompass safety factors that are intended to ensure that the natural variations in pipe dimensions and material properties that occur during the manufacture of a pipeline that could be 1000 km long will not undermine the capacity of the pipeline to withstand the external pressure without collapse occurring. However, the factors are based on the few previous available tests; the possibility of carrying out such tests on complete pipe joints during fabrication of the pipe are not realistic since the tests take a significant time to be set up and completed.

Only one joint of a pipeline needs to collapse to flood the whole line. It is therefore axiomatic that a long deep-water pipeline is more vulnerable to collapse than a short deep-water pipeline purely because there is a greater statistical probability in a long line of a single joint manufactured sufficiently out-of-specification to precipitate collapse. There is a direct analogy with "the weakest link in the chain" as regards pipeline failure due to external pressure collapse. Given that the codes of practice are based on the collapse test results of a small finite number of joints of line pipe, the design codes have to introduce a factor based on overall length to increase the wall thickness down the whole route simply to address the increased statistical exposure of a long line to a single fatally out-of-specification pipe joint.

There is thus a need for a test method that can replicate the effects of external pressure to cause the collapse of long pipelines and that is easy to set up and complete.

This invention is based on the recognition that the deformations that lead to external pressure collapse are uniform along the pipe and that therefore the occurrence of external pressure collapse will be the same for a ring cut from the pipe as for the complete joint length of pipe that is subjected purely to external pressure.

DISCLOSURE OF THE INVENTION

A first aspect of the invention comprises a method of testing pipes for use in making subsea pipelines, comprising:
  cutting a ring from one or more pipes of the type used to make the pipeline;
  forming flat, substantially parallel surfaces on the ends of the ring;
  providing means for measuring strain and deformation of the ring;
  mounting the ring in a pressure chamber such that the ends of the ring form seals with opposing walls of the chamber to isolate the inside of the ring from the outside;
  increasing the pressure outside the ring and measuring the strain and deformation on the ring as the pressure increases; and
  using the deformation and strain measurements to determine a wall thickness for pipes to be used for the pipeline.

Preferably, the means for measuring strain and deformation are sensors that are applied to the ring. It is particularly preferred that they are deployed on the inner surface of the ring.

The step of mounting the ring in the pressure chamber preferably includes providing seals between the ends of the ring and the walls of the chamber.

The step of increasing the pressure typically includes pumping pressurised fluid into the chamber around the outside of the ring.

The method can also comprise determining a comparison of pressure applied and maximum strain measured to detect the onset of accelerating non-linear reduction in ring diameter with increasing pressure.

The length of ring cut from the pipes is preferably selected such that the pipe still remains within tolerances for use in the pipeline. It is typically selected to be about twice the wall thickness.

A second aspect of the invention provides an apparatus for testing rings cut from pipes for use in making subsea pipelines, comprising:
  first and second test chamber sections which, when placed together define a test chamber for receiving the ring to be tested;

one or more sensors for measuring strain and deformation of the ring;

sealing means located in the chamber for forming a seal against the ring when received in the chamber;

means for clamping the first and second sections together to form the chamber and engage the sealing means against the ring when received in the chamber to form a pressure resistant seal between the inside and outside of the ring; and a fluid inlet port in one of the chamber sections to allow a pressurised fluid to be admitted to the chamber outside the ring when received in the chamber.

In one preferred embodiment, the first section defines a recess that is closed by the second section to form the chamber. The fluid inlet port is preferably formed in a wall of the first section.

The first and second sections can include inter-engaging formations such as spigots and recesses, to allow accurate location of one against the other when forming the chamber.

Seals can also be provided for the engaged surfaces of the first and second sections.

A bleed hole can be provided in one or other of the first and second sections to allow pressure equalisation between the inside of the ring and ambient pressure during testing.

In one embodiment, the clamping means comprises one or more screws which pass through holes in one section to extend through the chamber inside the ring and engage in threaded bores in the other section.

In another embodiment, the clamping means comprises a cylinder formed in one section which has a piston located therein, the piston extending from the cylinder through the chamber inside the ring and having an end fixed to the other section, a supply of driving fluid being connected to the cylinder which is operable to draw the fixed end of the piston towards the cylinder and clamp the two sections together.

The method and apparatus according to the invention has a number of advantages, including:

enabling tests to be carried at reasonable costs to provide a more comprehensive basis for design codes and calculations;

enabling a large number of tests to be carried out to determine the effects of variations in material properties and geometry of pipe prior to the design of a specific pipeline;

providing the basis for optimising the wall thickness of pipes intended for installation at specific depths and with specific equipment thus allowing cost reduction to be realised; and enabling tests to be carried out during fabrication of specific pipe to ensure the levels of safety against external pressure collapse are being maintained.

MODE(S) FOR CARRYING OUT THE INVENTION

Tests on long sections of individual pipe joints have shown that the deformations that lead to external collapse are uniform along the pipe. This observation is supported by theoretical studies and numerical modelling. The implication is that the occurrence of external pressure collapse will be the same for a ring cut from the pipe as for the complete joint length of pipe that is subjected purely to external pressure. The testing approach of the invention is therefore is based on cutting short sections from a pipe and machining the ring to a uniform length. The ring is placed in a rigid frame that allows the machined faces of the ring to be sealed such that a pressure can be applied only to the outer circular surface of the ring. The inner circular surface of the ring is maintained at ambient pressure and thus is suitable for attachment of devices to measure the strains and deformations that are caused by the pressure on the outer circular surface of the ring.

The seals on both machined flat faces of the ring are such that the pressure is constrained to be on the outer circular surface of the ring only and not on the flat machined faces. The seals are such that the ring is not subject to substantial forces parallel to the machined flat faces such that the deformations of the circular faces of the ring are impeded.

The pressure is applied from an external pump such that the pressure is increased or decreased by the addition or subtraction of a specified volume of fluid to or from the space surrounding the outer circular surface of the ring. This arrangement allows the radial deformations of the ring caused by the pressure on the outer cylindrical surface to increase or decrease in a controlled manner.

The action of the seals on the machined flat surfaces of the ring can be achieved by encasing the ring in a rigid block that is shaped to ensure that there is no deformation at the seals. An alternative arrangement is to have the space in which the seals operate adjustable and controlled by the action of a piston that is subjects to the same (or different) pressure as that applied to the outside cylindrical surface of the ring.

A typical test will involve the following steps:
a. Cut the ring from the pipe and machine the ends flat and parallel to within prescribed tolerances;
b. Fit attachments to measure the strains and deformations of the ring;
c. Fit the ring into the frame with the seals in place;
d. Apply pressure and ensure the seals are active and effective;
e. Increase the pressure, recording the strain and deformation measurements; and
f. Continue to increase the pressure until a maximum value is attained.

It may be useful to also plot a curve of pressure applied against maximum strain measured to detect the onset of an accelerating non-linear reduction in ring diameter with increasing pressure that is independent of any leakage of hydraulic fluid past the seals.

Figure 1:
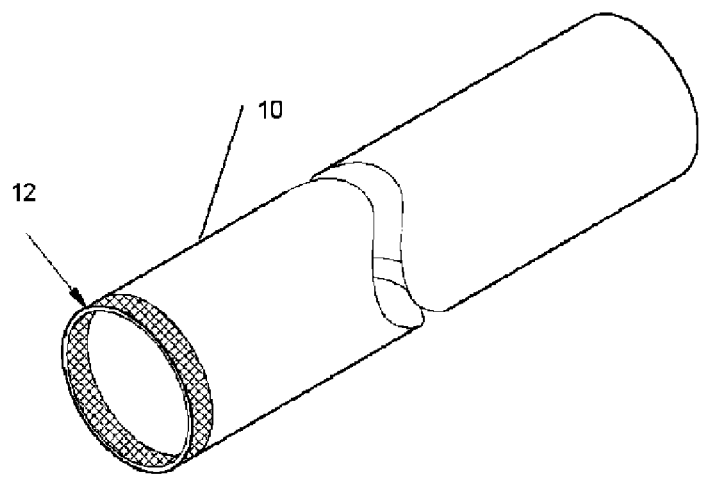
FIG. 1 shows a pipeline of the type for testing in accordance with the invention.
Figure 2:
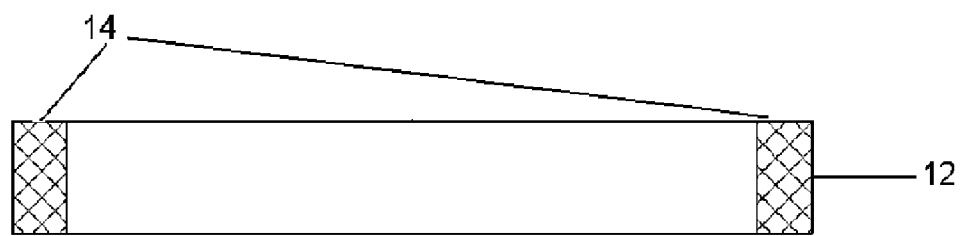
FIG. 2 shows a cross section of a test ring cut from the pipe of FIG. 1.

FIG. 1 shows a pipe 10 used in subsea pipelines. A typical example will be about 12.2 m long, have an external diameter of 508 mm and a wall thickness of 35 mm. The test ring 12 (also shown in FIG. 2) is cut from one end of the pipe and has a length of 70 mm, approximately twice the wall thickness. Even after this length of ring has been cut, the pipe 10 can still be used in construction of a pipeline. The end surfaces 14 of the ring 12 are machined so as to be substantially parallel and flat, for example a tolerance of +0 to −0.01 mm on the overall length of the ring is typical.

Figure 3:
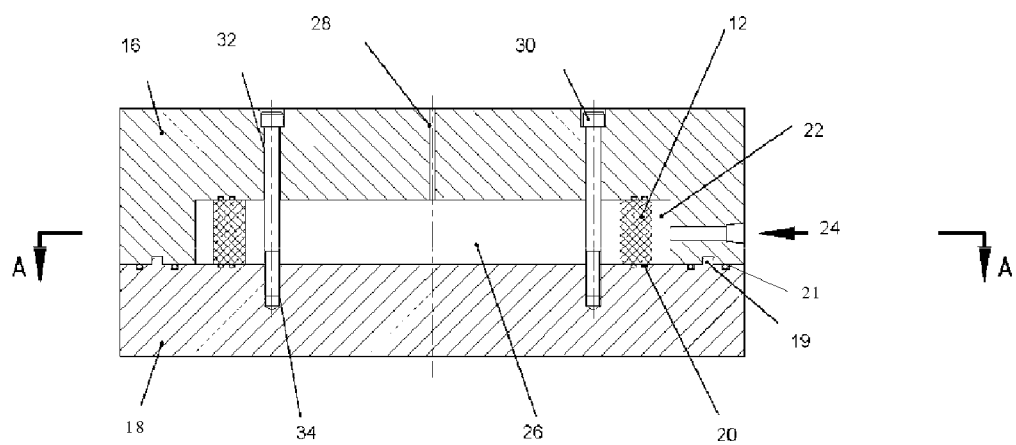
FIG. 3 shows a cross section of a test apparatus according to a first embodiment of the invention.
Figure 4:
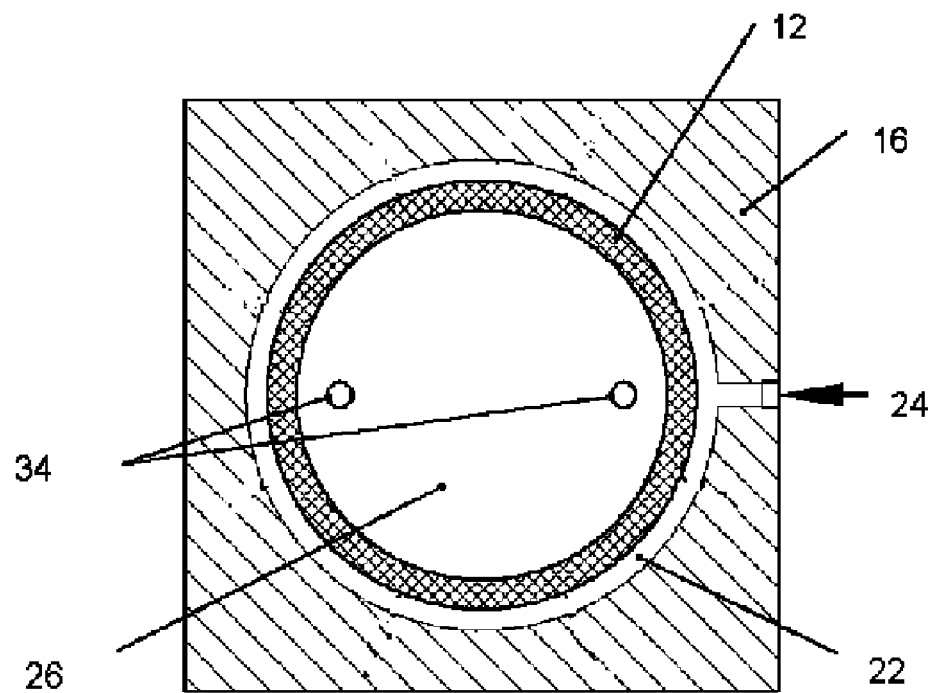
FIG. 4 shows a section on line A-A of FIG. 3.

FIGS. 3 and 4 show one embodiment of an apparatus according to the invention set up with a ring in place for testing. The test ring 12 is mounted between the top section 16 and lower section 18 which together define the test chamber. The two halves of the pressure test chamber 16, 18 are provided with locating spigots 19 which locate in corresponding locating holes with associated seals 21 to allow location of the two halves. O-ring or pressure-energised pressure containing seals 20 are provided in the top and bottom sections. These are engaged by the test ring 12 to form an annulus accessible by a supply of pressurised hydraulic test fluid through an appropriate inlet port 24. The central void 26 inside the test ring 12 is vented to atmosphere through a bleed hole 28 which is of sufficiently large diameter to also provide access for any instrumentation cabling to the strain gauges (not shown) on the inner cylindrical surface of the test ring 12.

The two halves 16, 18 are held together by mechanical sealing screws 30. The screws 30 extend though holes 32 in the top section 16 and pass through the void 26 to engage in threaded bores 34 in the bottom section 18. Two screws 30 are shown but any suitable number can be used to ensure proper clamping.

The force with which the two halves are held together is sufficient to make the annulus 22 pressure tight internally and externally against the pressure containing seals 20, 21. The tolerance with which the ring 12 is cut from the pipe is such that no leakage occurs from the annulus 22 into the void 26 whilst at the same time avoiding undue restraining friction on the radial movement inwards of the ring 12 outer diameter under hydraulic loading.

Figure 5:
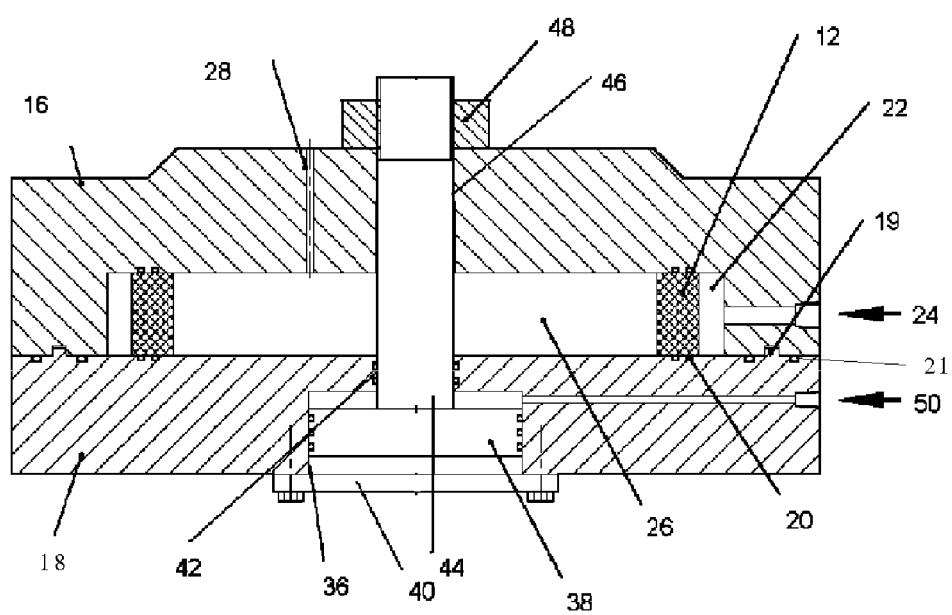
FIG. 5 shows a cross section of a test apparatus according to a second embodiment of the invention.

FIG. 5 shows a second embodiment of the test apparatus in which the clamping screws shown in FIGS. 3 and 4 are replaced by a hydraulic piston arrangement. A cylinder 36 is formed in the lower section 18 in which a piston 38 is slidably located. The outer end of the cylinder is closed by a plate 40. A bore 42 equipped with sliding seals extends from the inner end of the cylinder 36 to the void 26. A connecting rod 44 extends from the piston 38, through the bore 42 to a locating bore 46 in the top section 16 where it is fixed to a piston ring clamp 48. An inlet port 50 is provided at the lower end of the cylinder 36 to allow pressurised fluid to be admitted which drives the piston 38 along the cylinder 36 to clamp the top section 16 to the lower section 18.

Methods and apparatus according to the invention demonstrate a number of advantages over previous techniques. They allow testing of a representative sample of test rings taken from all the line pipe joints required for a long deepwater pipeline to give direct physical quantified evidence of the capacity of each of these specimens to resist external hydrostatic collapse. The collapse tolerance of each specimen test ring can be confidently held to be representative of the collapse tolerance of the joint from which it is cut. Use of the invention in the manner described can permit a reduction in the factor used currently in the design process to increase the wall thickness of the whole line based on the increasing exposure of the pipeline with increasing length to the increasing statistical probability of a single joint sufficiently out-of-specification to precipitate collapse. The joint from which each test ring is cut can still be utilized as a production joint and is not wasted. The net result can be a highly significant reduction in pipeline wall thickness that will provide improved commercial availability of line pipe and significant cost savings.

The invention claimed is:

1. A method of testing pipes for use in making subsea pipelines, comprising:
    cutting a ring from one or more pipes of the type used to make the pipeline;
    forming flat, substantially parallel surfaces on the ends of the ring;
    providing means for measuring strain and deformation of the ring;
    mounting the ring in a pressure chamber such that the ends of the ring form seals with opposing walls of the pressure chamber to isolate the inside of the ring from the outside such that pressure is applied only to the outside of the ring during testing;
    increasing the pressure outside the ring and measuring the strain and deformation on the ring as the pressure increases; and
    using the deformation and strain measurements to determine a wall thickness for pipes to be used for the pipeline.

2. A method as claimed in claim 1, wherein the step of providing means for measuring strain and deformation comprises applying sensors to the ring.

3. A method as claimed in claim 2 comprising deploying the sensors on the inner surface of the ring.

4. A method as claimed in claim 1, 2 or 3, wherein the step of mounting the ring in the pressure chamber includes providing seals between the ends of the ring and the walls of the pressure chamber.

5. A method as claimed in claim 1, wherein the step of increasing the pressure includes pumping pressurised fluid into the pressure chamber around the outside of the ring.

6. A method as claimed in claim 1, further comprising
    determining a comparison of pressure applied and maximum strain measured to detect the onset of accelerating non-linear reduction in ring diameter with increasing pressure.

7. A method as claimed in claim 1, comprising selecting the length of ring cut from the pipes such that the pipe still remains within tolerances for use in the pipeline.

8. A method as claimed in claim 7, comprising selecting the length to be about twice the thickness of the wall of the pipe.

9. Apparatus for testing rings cut from pipes for use in making subsea pipelines, comprising:
    first and second test chamber sections which, when placed together define a test chamber for receiving the ring to be tested;
    one or more sensors for measuring strain and deformation of the ring;
    sealing means located in the test chamber for forming a seal against the ring when received in the test chamber such that in use pressure is applied only to the outside of the ring;
    means for clamping the first and second test chamber sections together to form the test chamber and engage the sealing means against the ring when received in the test chamber to form a pressure resistant seal between the inside and outside of the ring; and
    a fluid inlet port in one of the test chamber sections to allow a pressurised fluid to be admitted to the test chamber outside the ring when received in the test chamber.

10. Apparatus as claimed in claim 9, wherein the first test chamber section defines a recess that is closed by the second test chamber section to form the test chamber.

11. Apparatus as claimed in claim 10, wherein the fluid inlet port is formed in a wall of the first test chamber section.

12. Apparatus as claimed in claim 9 or 10, wherein the first and second test chamber sections include inter-engaging formations to allow accurate location of one against the other when forming the test chamber.

13. Apparatus as claimed in claim 9, wherein seals are provided for the engaged surfaces of the first and second test chamber sections.

14. Apparatus as claimed in claim 9, further comprising a bleed hole in one of the first and second test chamber sections to allow pressure equalisation between the inside of the ring and ambient pressure during testing.

15. Apparatus as claimed in claim 9, wherein the clamping means comprises one or more screws which pass through holes in one test chamber section to extend through the test chamber inside the ring and engage in threaded bores in the other test chamber section.

16. Apparatus as claimed in claim 9, wherein the clamping means comprises a cylinder formed in one test chamber section which has a piston located therein, the piston extending from the cylinder through the test chamber inside the ring and having an end fixed to the other test chamber section, a supply of driving fluid being connected to the cylinder which is operable to draw the fixed end of the piston towards the cylinder and clamp the two test chamber sections together.

17. A method of testing pipes of subsea pipelines, the method comprising:
cutting a pipe ring from a pipe candidate to be used to construct a subsea pipeline;
forming flat, substantially parallel surfaces on the ends of the pipe ring;
mounting the pipe ring in a pressure chamber such that the ends of the pipe ring form seals with opposing walls of the pressure chamber to isolate the inside of the pipe ring from the outside of the pipe ring such that pressure is applied only to the outside of the pipe ring during testing;
increasing the pressure outside the pipe ring to simulate subsea pressure conditions;
measuring the strain and deformation on the pipe ring as the pressure outside of the pipe ring increases; and
determining the sufficiency of a wall thickness of the pipe candidate based on the deformation and strain measurements of the pipe ring.

18. A subsea pipe test apparatus comprising:
first and second test chamber sections coupleable together to define a test chamber sized to receive a ring section of a subsea pipe to be tested;
at least one sensor coupled to the ring section to measure strain and deformation of the ring section during testing;
a seal located in the test chamber to form a seal against the ring section when the ring section is received in the test chamber;
a clamping arrangement to clamp the first and second test chamber sections together to form the test chamber and urge the seal against the ring section when the ring section is received in the test chamber to form a pressure resistant seal between the inside and outside of the ring section; and
a fluid inlet port in one of the test chamber sections to allow a pressurised fluid to be admitted to the test chamber outside of the ring section when the ring section is received in the chamber.

* * * * *